(12) United States Patent
Grün et al.

(10) Patent No.: US 7,767,772 B2
(45) Date of Patent: Aug. 3, 2010

(54) SPHERICAL PARTICLES

(75) Inventors: Michael Grün, Hanau (DE); Klaus Heyne, Bruchköbel (DE); Claudine Mollenkopf, Frankfurt (DE); Sam Lee, Cumming, GA (US); Roger Uhrhammer, Aurora, IL (US)

(73) Assignee: Degussa AG, Duesseldorf (DE)

( * ) Notice: Subject to any disclaimer, the term of this patent is extended or adjusted under 35 U.S.C. 154(b) by 778 days.

(21) Appl. No.: 10/595,667

(22) PCT Filed: Nov. 3, 2004

(86) PCT No.: PCT/EP2004/012388

§ 371 (c)(1),
(2), (4) Date: Mar. 20, 2007

(87) PCT Pub. No.: WO2005/044873

PCT Pub. Date: May 19, 2005

(65) Prior Publication Data

US 2008/0262178 A1    Oct. 23, 2008

(30) Foreign Application Priority Data

Nov. 4, 2003    (DE) ................................ 103 52 138

(51) Int. Cl.
*C08F 4/42* (2006.01)

(52) U.S. Cl. ...................... 526/124.2; 526/210; 526/348

(58) Field of Classification Search .............. 526/124.2, 526/210, 348
See application file for complete search history.

(56) References Cited

U.S. PATENT DOCUMENTS

| | | | |
|---|---|---|---|
| 5,556,820 A | 9/1996 | Funabashi et al. | |
| 5,917,100 A | 6/1999 | Böhm et al. | |
| 5,965,478 A | 10/1999 | Goto et al. | |
| 2001/0012908 A1* | 8/2001 | Tanase et al. | ............... 568/851 |

FOREIGN PATENT DOCUMENTS

EP    0 461 268 A1    12/1991

\* cited by examiner

*Primary Examiner*—Ling-Siu Choi
(74) *Attorney, Agent, or Firm*—Smith Gambrell & Russell LLP

(57) ABSTRACT

Spherical particles comprising magnesium alcoholate and having a poured cone height of less than 17 mm are prepared by reacting magnesium, an alcohol or a mixture of various alcohols and a halogen and/or an optionally organic halogen compound with one another at below the boiling point of the alcohols.

The spherical particles are employed as a precursor for olefin polymerization catalysts.

8 Claims, 1 Drawing Sheet

SPHERICAL PARTICLES

CROSS-REFERENCE TO RELATED APPLICATIONS

This application claims the benefit of priority of German Patent Application No. 103 52 138.0 filed Nov. 4, 2003, and International Application No. PCT/EP2004/012388 filed Nov. 3, 2004, which are relied on and incorporated herein by reference.

INTRODUCTION AND BACKGROUND

The invention relates to spherical particles comprising magnesium alcoholates or a mixture of magnesium alcoholates, a process for their preparation and their use.

It is known to prepare magnesium alcoholate. Thus, US 2001/0012908 describes the synthesis of magnesium alcoholates at a temperature of 30 to 60° C.

U.S. Pat. No. 5,556,820 (date of application: Feb. 3, 1994, Idemitsu) describes the preparation of magnesium ethanolate from magnesium and ethanol in the presence of 0.019 to 0.06 gram-atom of halogen per mol of magnesium.

U.S. Pat. No. 5,965,478 (date of application: 13/08/1997, Toho Titanium) describes a magnesium ethanolate having a bulk density of 0.25-0.40 g/ml and a particle diameter of 1 to 100 μm as a component of a Ziegler-Natta catalyst. This is prepared by continuous or batchwise addition of alcohol and magnesium to a reaction mixture which is not defined in more detail. The synthesis takes place at the reflux temperature.

The flowability of the powder is of great importance for the processing and handling of pulverulent substances. During filling, transferring and emptying operations in particular, for example from barrels or other drums, a rapid flowing out of the magnesium alcoholate powder saves time and expenditure. A good flowability of the magnesium alcoholate powder must also be ensured because this class of substance is highly sensitive to air and water. Residues of substance in drums which have not been emptied completely are a high safety risk. Due to the good flowability, there is also a reduced risk of bridge formation when transferring to silos. Pneumatic delivery of the powder is also facilitated.

In the case of all the abovementioned known magnesium alcoholates, nothing is said about the flowability of the magnesium alcoholates formed here. There is therefore the need for a form of magnesium alcoholate powders which is distinguished by a good flowability.

The object of the invention is to prepare spherical particles comprising magnesium alcoholate or mixtures of magnesium alcoholates having a good flowability. These particles can serve, for example, as starting substance (catalyst precursor) for olefin polymerization catalysts.

SUMMARY OF THE INVENTION

The invention provides spherical particles comprising magnesium alcoholates or mixtures of magnesium alcoholates, which are characterized in that they have a poured cone height of less than 17 mm.

The lower the poured cone height, the better the flowability of the powder.

Measurement of the poured cone height under precisely defined conditions is a measure of the flowability of a pulverulent substance. The angle of repose is a further evaluation criterion for the flow properties. Since given the same base dimension the poured cone height depends directly on the angle of repose and is considerably easier to determine, this is determined.

Another method for determination of the flowability of powders is, for example, measurement of the discharge speed using a modified Pfrengle discharge funnel [DIN ISO 4324].

The invention also provides a process for the preparation of the spherical particles comprising magnesium alcoholates or mixtures of magnesium alcoholates according to the invention, which is characterized in that magnesium, an alcohol or a mixture of various alcohols and a halogen and/or a halogen compound are reacted with one another at below the boiling point of the alcohol component having the lowest boiling point, and the product obtained is separated off and dried.

The alcohol component having the lowest boiling point can have a boiling point of 68° C. It can be, for example, methanol.

BRIEF DESCRIPTION OF DRAWING

The invention will be further understood with reference to the accompanying drawing which illustrates measurement of poured cone height.

DETAILED DESCRIPTION OF THE INVENTION

Figure 1:
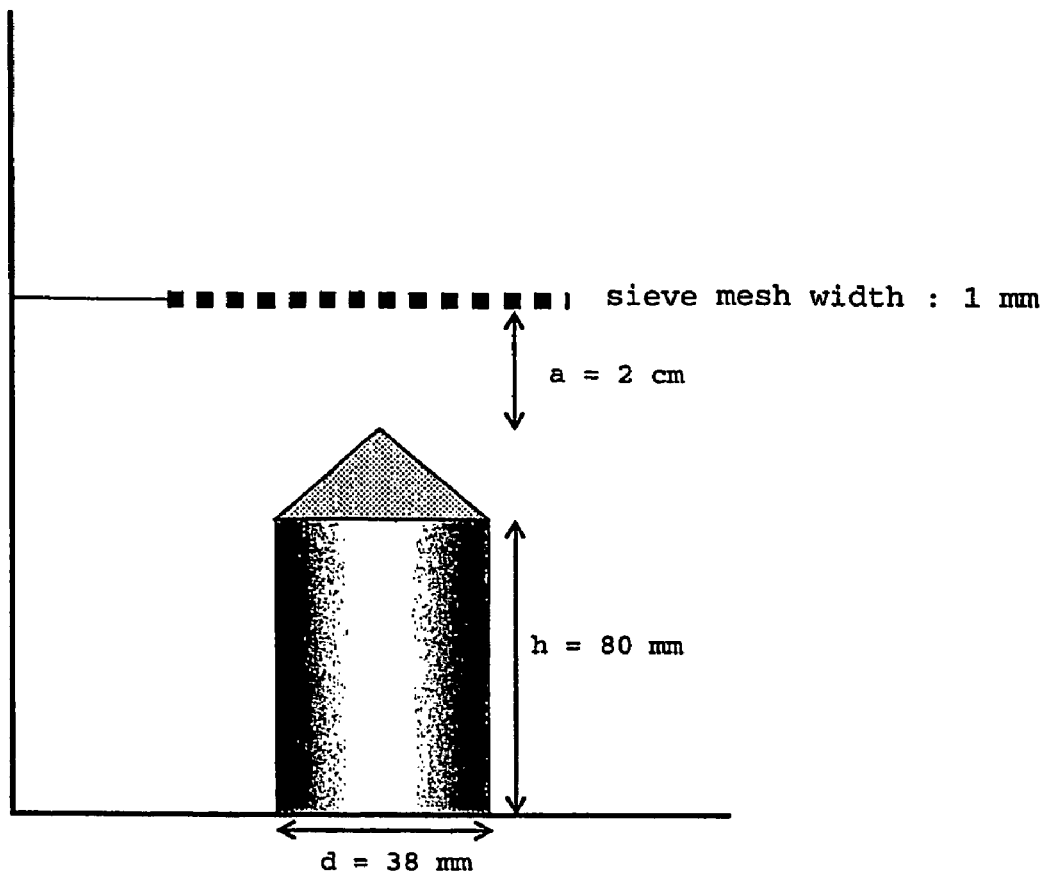
FIG. 1 shows a diagram of the poured cone height measurement.

The main constituent of the spherical particles according to the invention can in general be magnesium ethanolate. In the case of mixtures of magnesium alcoholates, the content of the other magnesium alcoholates (in addition to magnesium ethanolate) and of a halogen-containing constituent present can be between 0.001 wt. % and 15 wt. % (in each case based on the total weight).

Particularly preferred spherical particles are those for which a mixture of ethanol, methanol and isopropanol is employed as the alcohol mixture in the preparation and the contents of the alcoholates in the end product are as follows:

magnesium ethanolate>80 wt. % magnesium methanolate: 0.001-15 wt. % magnesium isopropanolate: 0.001-10 wt. % halogen or halogen-containing component: 0.001-10 wt. %

The spherical particles can comprise small amounts of free alcohols and furthermore $Mg(OH)_2$ and/or $MgCO_3$.

The magnesium can be employed in the form of strip, filings, granules or also powder. Magnesium which is not coated or coated only with a thin oxide/hydroxide layer is preferred.

Mono- and polyhydric alcohols which have a linear or branched carbon chain can be employed as alcohols for the synthesis. The alcohols can be aliphatic, aromatic or mixed aliphatic-aromatic. Alcohols having 1-10 carbon atoms are preferably employed.

Examples of the Alcohols are:

Methanol, ethanol, n-propanol, n-butanol, n-pentanol, n-hexanol, n-heptanol, n-octanol, n-nonanol, n-decanol.

2-Propanol, 2-butanol, 2-pentanol, 2-hexanol, 2-heptanol, 2-octanol, 2-nonanol, 2-decanol.

2-Ethylbutanol, 2-ethylhexanol, 4-methyl-2-pentanol, 3,3,5-trimethylpentanol, 4-methyl-3-heptanol.

Phenol, benzyl alcohol, 2-phenylethanol, 1-phenyl-1-propanol ethylene glycol, glycerol.

Ethanol is particularly preferred as the alcohol. If an alcohol mixture is employed, ethanol can be employed as the main constituent and methanol and isopropanol as secondary constituents.

Preferably the mixture of the alcohols can consist of

90±9 wt.-% of ethanol 1 to 10 wt.-% of methanol 1 to 10 wt.-% of isopropanol

To facilitate the reaction, however, alcohols having a water content of <1,000 ppm are preferred. Otherwise, hydroxide layers form on the magnesium, as a result of which the reaction is slowed down.

The molar ratio of the alcohol or alcohol mixture (calculated as the sum of the moles of the individual constituents of the alcohol mixture) to magnesium can be between 1 and 100. It can be particularly preferably between 3 and 20.

A non-limiting selection for the halogen or the halogen-containing component is:

Iodine, bromine, chlorine, magnesium chloride, magnesium bromide, magnesium iodide.

Magnesium alkoxyhalides, such as, for example, magnesium ethoxyiodide, magnesium methoxyiodide, magnesium isopropoxyiodide, hydrogen chloride, chloroacetyl chloride and organic acid halides such as benzoyl chloride, phthaloyl chloride, acetyl chloride, propionyl chloride, butyryl chloride, trimethylacetyl chloride, trifluoroacetyl chloride, and chloroacetyl chloride.

Accordingly, the halogen compound can be an organic acid chloride. The acid chloride can be a chloroacetyl chloride.

Chloroacetyl chloride, iodine, magnesium iodide and magnesium chloride as well as magnesium alkoxyhalides are particularly preferred.

Mixtures of the abovementioned substances can also be employed.

The halogens or halogen-containing substances can be employed in the reaction both in the pure state and in the form of solutions. The halogen or the halogen-containing components can also be present in a chemically modified form after the reaction. Thus, for example, after the reaction iodine can be present partly as magnesium iodide and/or magnesium alkoxyiodide.

The reaction can be carried out at a reaction temperature of between 0° C. and 67° C., it also being possible for the reaction temperature to be changed during the reaction. The particle size can be determined by the choice of the reaction temperature.

The pressure can be between 0.001 and 100 bar. The reaction can preferably be carried out under atmospheric pressure.

The sequence of the addition of the reaction partners can be as desired. The following reaction procedure is particularly preferred:

1) Initial introduction of the alcohol mixture and magnesium into the reaction vessel
2) Addition of the halogen component The end of the reaction can be recognized by the evolution of hydrogen stopping. The reaction time can in general be 5-50 h.

After the reaction, the product can be washed again, for example with the alcohol mixture used for the preparation, in order to adjust the content of halogen or halogen-containing component.

The molar ratio of the halogen or halogen component to magnesium at the start of the reaction can be between 0.0001 and 0.5. In the end product, it can be between 0.000001 and 0.5.

The average particle diameter ($d_{50}$) of the spherical particles according to the invention can be between 1 and 200 µm. The particle diameter is particularly preferably between 10 and 50 µm.

The span, which describes the width of the particle size distribution, is in general below 4, particularly preferably below 1.5, the span being determined according to the following formula.

$$\text{span} = \frac{d_{90} - d_{10}}{d_{50}}$$

The form of the particles can preferably be spherical.

The specific surface area can be between 2 and 100 $m^2/g$.

The specific pore volume is between 0.01 ml/g and 4 ml/g.

The bulk density can be at least 0.25 $g/cm^3$. The tapped density can be at least 0.35 $g/cm^3$.

The spherical particles according to the invention can be employed as a precursor for olefin polymerization catalysts, thus, for example, as a catalyst support precursor.

EXAMPLES

The specific surface area is determined by nitrogen absorption at 77 K in accordance with DIN 66131 (calculation according to the BET model).

The specific pore volume is measured by mercury intrusion to 2,000 bar in accordance with DIN 66133.

The particle size distribution is measured with a Microtrac-X100 apparatus from Microtrac in accordance with the principle of laser diffraction using unified scatter technique. The apparatus is equipped with one primary (on-axis) laser diode and two secondary (off-axis) laser diodes with one forward and one high-angle photo detector array. The range is 0.04-704 micron. The sample is suspended in ethanol before the measurement. Ultrasound was applied for 60 seconds before measurement.

Alternatively a Horiba LA-920 was used. In this case the samples were suspended in isopropanol and subjected to ultrasound for 60 seconds. A circulation speed of 7 was used before measurement.

The bulk density and the tapped density are determined as follows:

Determination of the Bulk Density (Method A)

For determination of the bulk density, a given volume of the powder is poured through a funnel into a measuring beaker and its weight is determined.

Determination of the Tapped Density (Method B)

For determination of the tapped density, a given volume of the powder is poured through a funnel into a measuring beaker and vibrated and its weight is determined.

Equipment:

*Balance with an error limit of ±0.1 g

*Filling funnel with a volume of about 200 $cm^3$

*Cylindrical measuring beaker of approx.

100 $cm^3$±0.5 $cm^3$

*Sheet of paper

Sampling and Pretreatment of the Sample:

Two samples are taken from the magnesium alcoholate powder to be tested, which is in the delivery state. The samples are tested under a nitrogen atmosphere. In the event of deviations of greater than 0.03 g/cm$^3$, a triplicate determination is carried out as a control.

Procedure:

Bulk Density:

The measuring beaker is tared on a balance and covered with a sheet of paper. Thereafter, the filling funnel is placed on the paper. A sample of approx. 150 cm$^3$ is loosely introduced into the filling funnel. The paper is then removed, so that the sample falls into the measuring beaker. If necessary, the flow of the sample can be assisted by stirring with a rod (or spatula). The powder mass piled up above the upper edge of the measuring beaker is skimmed off with a straight-edged blade or ruler at an angle of 45° with respect to the piled-up powder mass. The measuring beaker filled with the powder is weighed to 0.1 g and the weight (weight of magnesium alcoholate powder) is recorded.

Evaluation:

The bulk density is calculated according to the numerical value of bulk density=weight determined/100 (in g/cm$^3$ or g/ml). The arithmetic mean—in addition to the individual values—of the two determinations is to be stated as the result of the test.

Tapped Density:

The measuring beaker is tared on a balance and covered with a sheet of paper. Thereafter, the filling funnel is placed on the paper. A sample of approx. 150 cm$^3$ is loosely introduced into the filling funnel. The sheet of paper is then removed, so that the sample falls into the measuring beaker. If necessary, the flow of the sample can be assisted by stirring with a rod (or spatula). Thereafter, the contents of the measuring beaker are vibrated (measuring beaker vibrated and tamped) until the powder cannot be compressed further. During this operation, the measuring beaker is constantly topped up with sample material.

The powder mass piled up above the upper edge of the measuring beaker is skimmed off with a straight-edged blade or ruler at an angle of 45° with respect to the piled-up powder mass. The measuring beaker filled with the powder is weighed to 0.1 g and the weight (weight of magnesium alcoholate powder) is recorded.

Evaluation:

The tapped density is calculated according to the numerical value equation of tapped density=weight determined/100 (in g/cm$^3$ or g/ml). The arithmetic mean—in addition to the individual values—of the two determinations is to be stated as the result of the test.

The alcoholate contents in the end products are determined by hydrolysis of the alcoholate mixtures with acid. After neutralization, the alcohols released are determined by gas chromatography (HP 5890 gas chromatograph with DB 624 as the stationary phase, 2-butanol as the internal standard).

The halogen content is determined by potentiometric titration after hydrolysis of the sample with ethanol/acetic acid (Metrohm Titroprocessor 682, indicator electrode: silver rod, reference electrode Ag/AgCl/0.1 M HClO$_4$)

The poured cone height is determined as follows:

A: Test equipment:

Metal sieve (mesh width: 1 mm)

Vernier

Metal solid cylinder, d=38 mm, h=80 mm

Scraper

B. Test Substances:

Sample material

Procedure:

The wire sieve is fixed to the stand approx. 10 cm above the metal solid cylinder. To establish the final height of the sieve, the powder is poured slowly on to the sieve and carefully passed through the sieve by means of the scraper. The distance from the sieve to the poured cone tip of the powder is then adjusted to 2 cm. When the poured cone of the powder is uniform in shape, sieving of the powder is ended and the poured cone height is read off at the tip of the cone with the surface gauge.

Evaluation:

The poured cone height is stated in mm.

Precision:

The reading error of the poured cone height is 01.1 mm. The average deviation of repeated measurements on a sample is 0.2 mm.

Test Methods for Catalyst and Polymer

MFR: Polymer melt flow rate is measured according to ASTM 1238.

Bulk Density Polymer powder bulk density is measured according to ASTM D1895B.

Catalyst particle size distribution: Spherical magnesium ethoxide material and catalyst particle size distributions are measured using a Malvern Mastersizer™ X.

Polymer particle size distribution: Polypropylene powder particle size distribution and fines are measured using a Malvern Mastersizer™ S.

Examples

Preparation of Magnesium Alcoholate Support Materials

Typical experimental procedure for examples 1 to 4

Magnesium and the alcohol mixture are initially introduced into a 2 l stirred container. Thereafter, a solution of iodine alcohol mixture is added. The reaction mixture is heated, while stirring, until the evolution of hydrogen has stopped. The product is filtered off over a pressure filter and dried in a rotary evaporator.

|  | Example 1 | Example 2 | Example 3 | Example 4 |
|---|---|---|---|---|
| Magnesium [g] | 145.0 | 105.0 | 145.0 | 145.0 |
| Iodine [g] | 10.78 | 15.68 | 10.78 | 10.78 |
| Alcohol mixture [g] | 1549.5 | 1549.5 | 1549.5 | 1549.5 |
| Wt. % (EtOH) | 91.2 | 89.5 | 91.2 | 91.2 |
| Wt. % (MeOH) | 3.5 | 5.2 | 3.5 | 3.5 |
| Wt. % (i-PrOH) | 5.3 | 5.3 | 5.3 | 5.3 |
| Wt. % (iodine) based on magnesium | 7.5 | 14.8 | 7.4 | 7.4 |
| Reaction temperature [° C.] | 50 | 50 | 50 | 50 |
| $d_{10}$ [μm] | 3.8 | 12.2 | 21.5 | 4.0 |
| $d_{50}$ [μm] | 18.6 | 25.0 | 30.5 | 22.7 |
| $d_{90}$ [μm] | 25.5 | 35.9 | 43.2 | 30.7 |
| Span | 0.71 | 0.95 | 0.71 | 1.18 |
| Bulk density [g/ml] | 0.43 | 0.39 | 0.44 | 0.42 |
| Tapped density [g/ml] | 0.54 | 0.49 | 0.58 | 0.55 |

-continued

|  | Example 1 | Example 2 | Example 3 | Example 4 |
|---|---|---|---|---|
| Poured cone height [mm] | 12.5 | 13.3 | 15.6 | 13.4 |
| methanol after hydrolysis [wt. %] | 7.0 | 9.8 | 4.1 | 4.6 |
| isopropanol after hydrolysis [wt. %] | 1.4 | 0.86 | 1.9 | 1.5 |
| Content of iodine [wt. %] | 0.63 | 0.89 | 0.37 | 0.7 |

Comparative Example 1

Use of Pure Ethanol, Chloroacetyl Chloride as Catalyst

A 2-L Buchi glass reactor is equipped with an overhead stirrer with a paddle-type agitator on the bottom of the shaft and a U-shaped agitator staggered directly above the paddle. The reactor is charged with absolute ethanol (930 mL, 99.5%, Aldrich), magnesium turnings (40 g), then chloroacetyl chloride (10.0 mL), all under a nitrogen blanket. The stirrer is set to 200 rpm and the reaction is allowed to proceed without temperature control. After 63 hours of stirring, a mixture of needle-like crystals and a flocculent solid is obtained. The solid is unsuitable for converting into a propylene polymerization catalyst. The poured cone height of this material is 24.9 mm. The particle properties were as follows:

| $d_{10}$ [μm] | 5.4 |
|---|---|
| $d_{50}$ [μm] | 45.8 |
| $d_{90}$ [μm] | 183.1 |
| Span | 3.88 |

Comparative Example 2

According to U.S. Pat. No. 5,965,478, Toho Titanium 5 g magnesium is added to 0.5 g iodine in 100 g ethanol. The mixture is heated to reflux temperature (78° C.). 8 portions of 2.5 g Mg and 25 g ethanol are added to this mixture every 5 minutes while the temperature is kept at 78° C. (boiling point of ethanol). Excess ethanol is removed and the poured cone height of the dried product is found to be 19.2 mm. The particle parameters are:

| $d_{50}$ [μm] | 42.9 |
|---|---|
| $d_{10}$ [μm] | 16.4 |
| $d_{90}$ [μm] | 70.7 |
| Span | 1.27 |

Comparative Example 3

Hy 103

21.8 g magnesium and 275 ml ethanol are filled into a reaction vessel. A solution of 1.62 g iodine in 25 ml ethanol is added. The mixture is stirred under reflux (78° C.) for 20 hours. Excess ethanol is removed and the poured cone height of the dried product is found to be 40.8 mm. The particle parameters are:

| $d_{50}$ [μm] | 11.0 |
|---|---|
| $d_{10}$ [μm] | 3.2 |
| $d_{90}$ [μm] | 44.4 |
| Span | 3.74 |
| Content of iodine [wt. %] | 1.0 |

Comparative Example 4

Commercially available magnesium ethanolate from Degussa (d50≈700 μm) is ground to an average particle diameter of 25.0 μm with a CSM 165 sifter mill (Netzsch). Measurement of the poured cone height gives a value of 19.8 mm.

Comparative Example 5

Commercially available magnesium ethanolate from Degussa (d50≈700 μm) is ground to an average particle diameter of 5.2 μm with an AFG 100 fluidized bed counter-jet mill (Hosokawa Alpine). Measurement of the poured cone height gives a value of 19.0 mm.

Propylene Polymerizations, Gas Phase.

Gas phase polymerizations are performed in a horizontal, cylindrical reactor measuring 10 cm in diameter and 30 cm in length with a volume of approximately one gallon (3.8 L). The reactor is operated in a continuous fashion. The reactor is equipped with an off-gas port for recycling reactor gas through a condenser and back through a recycle line to the nozzles in the reactor. In the reactor, liquid propylene is used as a quench liquid. The catalyst is introduced as a 0.5 to 1.5 wt % slurry in hexane through a liquid propylene-flushed catalyst addition nozzle. A mixture of organosilane compound and trialkylaluminum in hexane are fed separately to the reactor through a different liquid propylene-flushed addition nozzle. For all polymerizations the Al/Mg molar ratio of 6 and the Al/Si molar ratio of 6 is used.

During operation, polypropylene powder is passed over a weir and discharged through a powder discharge system. The polymer bed in the reactor is agitated by paddles attached to a longitudinal shaft within the reactor that is rotated at about 50 rpm. The reactor pressure is maintained at 300 psig (2.2 MPa). Reactor temperature is maintained at 160 F=71° C. Polymers with targeted melt flow rates are obtained by varying the amount of hydrogen in the reactor. Gas composition in the system is monitored via an on-line process gas chromatograph. Ethylene content in the reactor is adjusted by a mass-flow meter to vary the ethylene content in the final polymer. Ethylene content in the gas composition is monitored via the same on-line process gas chromatograph. The production rate is typically about 200-250 g/hour in order to maintain a stable process.

Example 5

MGE catalyst support (10 g, example 3) is suspended in 200 mL of heptane and transferred under nitrogen to a 1-liter jacketed glass reactor fitted with an overhead stirrer. The heptane is removed by decantation. Toluene (125 mL) is added and the slurry is stirred for 1 minute. The stirrer is turned off and the solid is allowed to settle for 1 minute. The toluene is removed by decantation. Next, 125 mL more of toluene is added, and the stirrer is started. TiCl$_4$ (105 mL, Akzo) is added slowly. The reactor contents are warmed to 57 C and mixed for an additional 30 minutes. The temperature is increased and as the temperature reached 100 C, 1.3 mL of di-n-butylphthalate (DNBP) is added and the reaction mixture stirred at 100 C for an additional 90 minutes. The stirrer is stopped and the liquid is removed by filtration through a small filter disk inserted into the slurry. After most of the liquid is removed, 125 mL of toluene and 105 mL of TiCl$_4$ are added and the slurry stirred at 100 C for 30 minutes. The stirrer is stopped, the solid is allowed to settle, and the liquid is removed through the filter disk. An additional 105 mL of TiCl$_4$ is added and the slurry stirred for 30 minutes at 100 C. The liquid is removed by filtration and 150 mL of heptane is added. The slurry is stirred at 57 C, the solid is then allowed to settle, and the heptane is removed. Four more warm heptane washes are done in the same way. The resulting solid had a uniform particle size and shape. The particle size distribution of the catalyst is: $d_{10}$=21.80, $d_{50}$=33.24, $d_{90}$=45.69 microns, span=0.71. Using diisobutyldimethoxysilane as the organosilane compound, a 6.6 MFR random copolymer containing 3.2 wt % ethylene is obtained. The yield is 33,100 g PP/g catalyst, the copolymer powder had a bulk density of 0.40 g/cc, and there are low fines (<1% under 150 microns).

Example 6

MGE catalyst support (example 4) is made in a similar manner as described in Example 3, except that some of the alcohol mixture is made up of recycled alcohol mixture from a previous support preparation. The support is converted to a catalyst in a similar manner as described in Example 5. The particle size distribution of the catalyst is: $d_{10}$=3.87, $d_{50}$=21.32, $d_{10}$=32.93 microns, span=1.36. Using diisobutyldimethoxysilane as the organosilane compound, a 3.2 MFR polypropylene is obtained. The yield is 24,500 g PP/g catalyst, the polymer powder had a bulk density of 0.46 g/cc, and there are low fines (1.1% under 150 microns). The average particle size is 1150 microns and the span is 1.2.

The invention claimed is:

1. Spherical particles comprising a mixture of magnesium alcoholates, wherein said particles have sufficient flowability so as to exhibit a poured cone height of less than 17 mm.

2. Spherical particles according to claim 1, wherein magnesium ethanolate is the main constituent.

3. Spherical particles according to claim 1 having the composition:
   magnesium ethanolate>80 wt. %,
   magnesium methanolate 0.001-15 wt. %,
   magnesium isopropanolate 0.001-10 wt. %
   halogen or halogen containing compound 0.001-10 wt. %.

4. A process for the preparation of the spherical particles according to claim 1, comprising reacting magnesium, an alcohol or a mixture of various alcohols and a halogen and/or halogen containing compound with one another at below the boiling point of the alcohol having the lowest boiling point, and separating the resulting the product obtained.

5. The process according to claim 4, further comprising drying the product.

6. The process of claim 4 wherein the halogen compound is an organic acid halide.

7. The process of claim 6 wherein the organic acid halide is chloroacetyl chloride.

8. A method for olefin polymerization comprising carrying out polymerization of an olefin in the presence of the spherical particles of claim 1.

* * * * *